United States Patent
Campagna

(10) Patent No.: US 11,076,817 B2
(45) Date of Patent: Aug. 3, 2021

(54) METHOD AND APPARATUS FOR SUBSTANTIALLY ARTIFACT-FREE ANATOMIC POSITIONING

(76) Inventor: Michael Campagna, Oak Park, IL (US)

( * ) Notice: Subject to any disclaimer, the term of this patent is extended or adjusted under 35 U.S.C. 154(b) by 1505 days.

(21) Appl. No.: 13/251,985

(22) Filed: Oct. 3, 2011

(65) Prior Publication Data

US 2012/0138065 A1 Jun. 7, 2012

Related U.S. Application Data

(60) Provisional application No. 61/389,271, filed on Oct. 3, 2010.

(51) Int. Cl.
*A61B 6/04* (2006.01)
*A61B 5/055* (2006.01)

(52) U.S. Cl.
CPC .............. *A61B 6/04* (2013.01); *A61B 5/055* (2013.01)

(58) Field of Classification Search
CPC ......... B32B 27/12; B32B 27/04; B32B 27/02; B32B 5/12; B32B 5/26; A61B 19/20; A61B 19/203; A61B 5/0555; A61B 6/04; A61B 6/0407
USPC ......... 128/845–846; 378/180, 195, 204, 208, 378/179; 5/621, 623–624, 601
See application file for complete search history.

(56) References Cited

U.S. PATENT DOCUMENTS

| | | | | |
|---|---|---|---|---|
| 2,605,152 A | * | 7/1952 | Krewson | A61G 13/12 108/152 |
| 3,124,328 A | * | 3/1964 | Foster | A47C 1/03 248/118 |
| 3,648,305 A | * | 3/1972 | Ersek | A61B 6/4283 378/180 |
| 3,947,686 A | * | 3/1976 | Cooper | A61B 6/0442 378/209 |
| 4,540,624 A | * | 9/1985 | Cannady, Jr. | 442/246 |
| 5,624,386 A | * | 4/1997 | Tailor | A61F 5/01 428/110 |
| 5,697,164 A | * | 12/1997 | Hausmann | A61B 5/1071 33/512 |
| 5,742,962 A | * | 4/1998 | Yoshino | A61B 6/0421 5/600 |
| 5,940,912 A | * | 8/1999 | Keselman | A61G 13/1235 297/411.35 |
| 6,374,438 B1 | * | 4/2002 | Fox | A61G 7/0507 5/600 |
| 6,626,408 B1 | * | 9/2003 | Lorbiecki | A61B 6/0421 248/279.1 |
| 6,925,668 B2 | * | 8/2005 | Cuschieri | A61B 90/60 5/621 |
| 8,322,342 B2 | * | 12/2012 | Soto | A61G 13/12 128/845 |

(Continued)

*Primary Examiner* — Ophelia A Hawthorne
*Assistant Examiner* — Camtu T Nguyen
(74) *Attorney, Agent, or Firm* — AddyHart P.C.

(57) ABSTRACT

A technique of forming a joint employing laminar sheeting is provided. At least a portion of the laminar sheeting includes a material that is substantially artifact-free such that the joint causes little imaging artifacts when medically imaged over at least a portion of the laminar sheeting including the rotational axis of said joint, which is at least useful for variable angular articulation of at least one anatomic supporting member joined to the joint and the normal anatomic positioning of at least one anatomic supporting member during normal anatomic positioning use.

48 Claims, 4 Drawing Sheets

(56) References Cited

U.S. PATENT DOCUMENTS

| | | | | |
|---|---|---|---|---|
| 2001/0039680 A1* | 11/2001 | Boucher | ............... | A61G 13/12 |
| | | | | 5/623 |
| 2002/0032927 A1* | 3/2002 | Dinkler | ............... | A61B 6/0442 |
| | | | | 5/601 |
| 2006/0123546 A1* | 6/2006 | Horton | .................. | A61G 13/08 |
| | | | | 5/613 |
| 2006/0242765 A1* | 11/2006 | Skripps et al. | .................. | 5/621 |
| 2007/0123857 A1* | 5/2007 | Deffenbaugh | ....... | A61B 17/025 |
| | | | | 606/54 |
| 2008/0104845 A1* | 5/2008 | Lee | ........................ | B29C 33/60 |
| | | | | 29/898.043 |
| 2008/0203249 A1* | 8/2008 | Priest | ................... | A61F 5/3761 |
| | | | | 248/118 |
| 2008/0260107 A1* | 10/2008 | Falbo | .................. | A61B 6/0442 |
| | | | | 378/208 |

\* cited by examiner

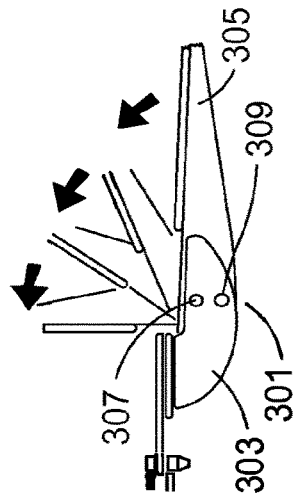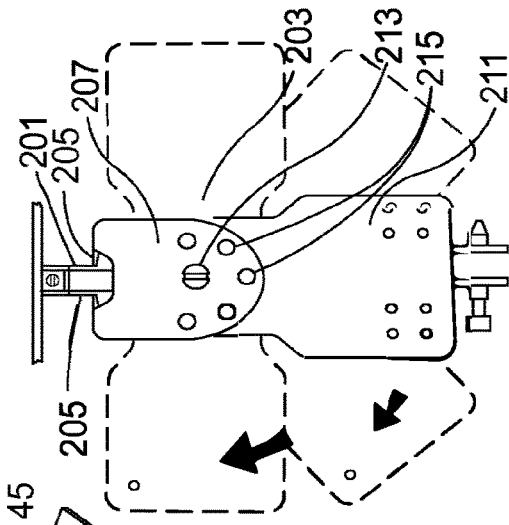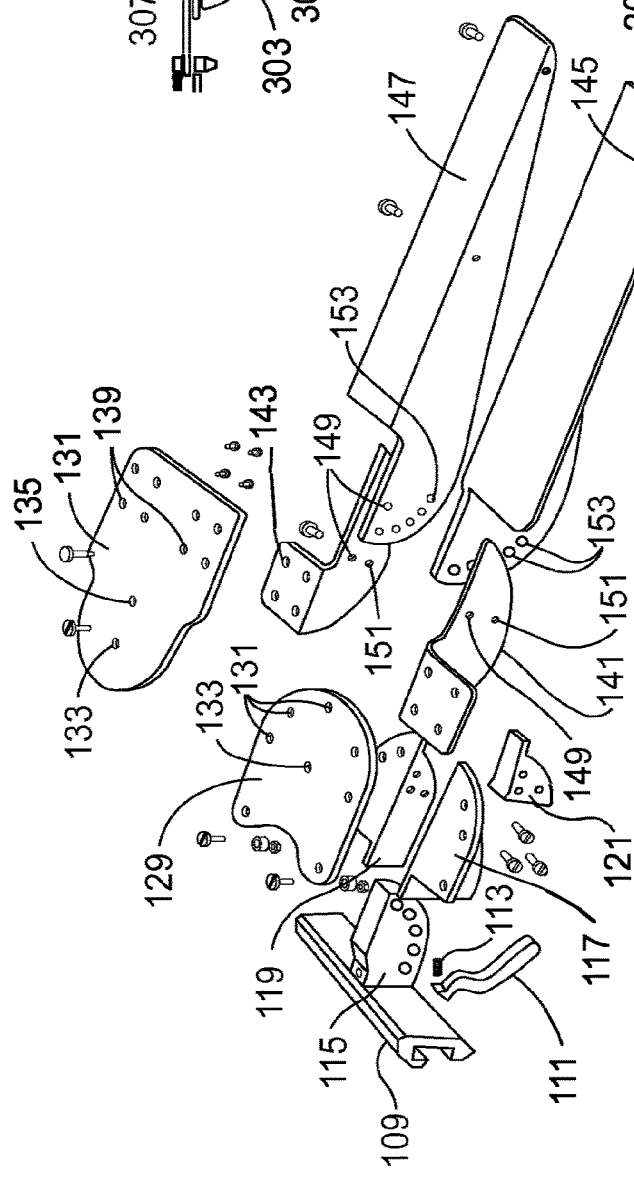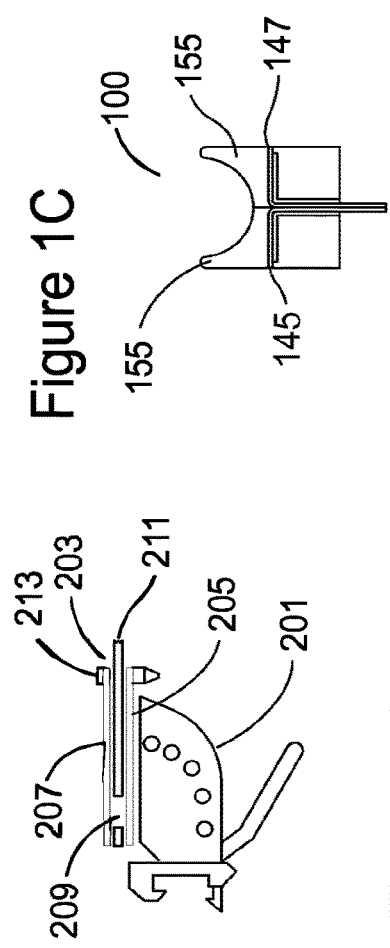

METHOD AND APPARATUS FOR SUBSTANTIALLY ARTIFACT-FREE ANATOMIC POSITIONING

CROSS-REFERENCE TO RELATED APPLICATIONS

The present Utility patent application claims priority benefit of the U.S. provisional application for patent Ser. No. 61/389,271 filed on 3 Oct. 2010 under 35 U.S.C. 120 and entitled "Method and Apparatus for Achieving Variable Radiolucent Anatomic Positioning Via the Usage of Non Metallic, Articulating, Variably Positioning, an Lockable Interconnecting Radiolucent Joints", under 35 U.S.C. 119 (e). The contents of this related provisional application are incorporated herein by reference for all purposes to the extent that such subject matter is not inconsistent herewith or limiting hereof.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to anatomical positioning in a medical environment. More particularly, the invention relates to articulating artifact free anatomical positioning.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Anatomical positioning is often used in the environments of medical, diagnostic and surgical patient imaging performed using magnetic or radiographic based data collection solutions. Magnetic solutions to medical imaging include, without limitation, Magnetic Resonance Imaging (MRI), which uses strong magnetic fields to align atomic nuclei within the patient's tissues and then to disturb the axis of rotation of these nuclei in order to render data into useful medical images. Radiographic solutions to medical imaging include, without limitation, X-Ray, Fluoroscopy (C-Arm), Computed Assisted Tomography (CT or CAT), Megavoltage Cone Beam Computer Assisted Tomography (i.e., MV-CBT, CBCT, or O-Arm), as well as Image Guided Radiotherapy (IGRT) and Positron Emission Tomography (PET Scans), all of which utilize ionizing radiation in order to generate medical images.

In the field of radiographic and magnetic medical imaging, the proximity of metallic components to the imaging array can be detrimental as metals are a prime source of imaging distortion and degradation, referred to herein as artifact. Within this environment, metal components typically fall into one of two subcategories. These categories are ferromagnetic metals and non-ferromagnetic metals. The category of ferromagnetic metals comprise metals that can possess a magnetic field including, without limitation, iron, nickel and cobalt. The category of non-ferromagnetic metals comprises metals that do not have a magnetic field and includes, without limitation, stainless steel, aluminum, copper, as well as various alloys. Within the MRI environment, the presence of ferromagnetic metals can lead to catastrophic and lethal mishaps due to the action of the extremely powerful imaging magnets acting upon ferromagnetic implements within the environment, which may attract said ferromagnetic objects at high velocities transforming them into projectiles. Non-ferromagnetic metals within proximity to a magnetic imaging array can cause distortion of field uniformity in the magnetic imaging array. It is believed that this distortion of field uniformity can cause artifacts that may render the images obtained as clinically unusable. In the field of radiographic imaging, the presence of ferromagnetic and non-ferromagnetic metals in proximity to the imaging apparatus can result in a streak artifacts. One can expect that streak artifacts may degrade the quality of clinical and diagnostic medical images and may render these images clinically unusable.

By way of educational background, an aspect of the prior art generally useful to be aware of is that a variety of limb positioners in the form of armboards and leg holders are currently available within the medical community. Said limb positioners generally attach to operating room tables, imaging platforms, or various patient platforms for purposes of facilitating surgery. With respect to the field of patient imaging, some of these current armboards and limb positioners purport to be radiolucent, at least to some extent. It is believed that currently available radiolucent positioners that provide variable positioning with or without locking means utilize metal components, typically non-ferromagnetic, in their construction for strength, which may result in the appearance of metallic artifacts in the images which are produced.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 1A, 1B and 1C illustrate an exemplary radiolucent anatomical positioner with articulating joints, in accordance with an embodiment of the present invention. FIG. 1A is a diagrammatic side view of the positioner attached to a patient platform. FIG. 1B is a diagrammatic front view, and FIG. 1C is an exploded view;

FIGS. 2A and 2B illustrate an exemplary articulating vertical base joint and an exemplary articulating horizontal joint, in accordance with an embodiment of the present invention. FIG. 2A is a diagrammatic side view, and FIG. 2B is a diagrammatic top view;

FIG. 3 is a diagrammatic side view of an exemplary articulating vertical joint, in accordance with an embodiment of the present invention.

Figure 1A:
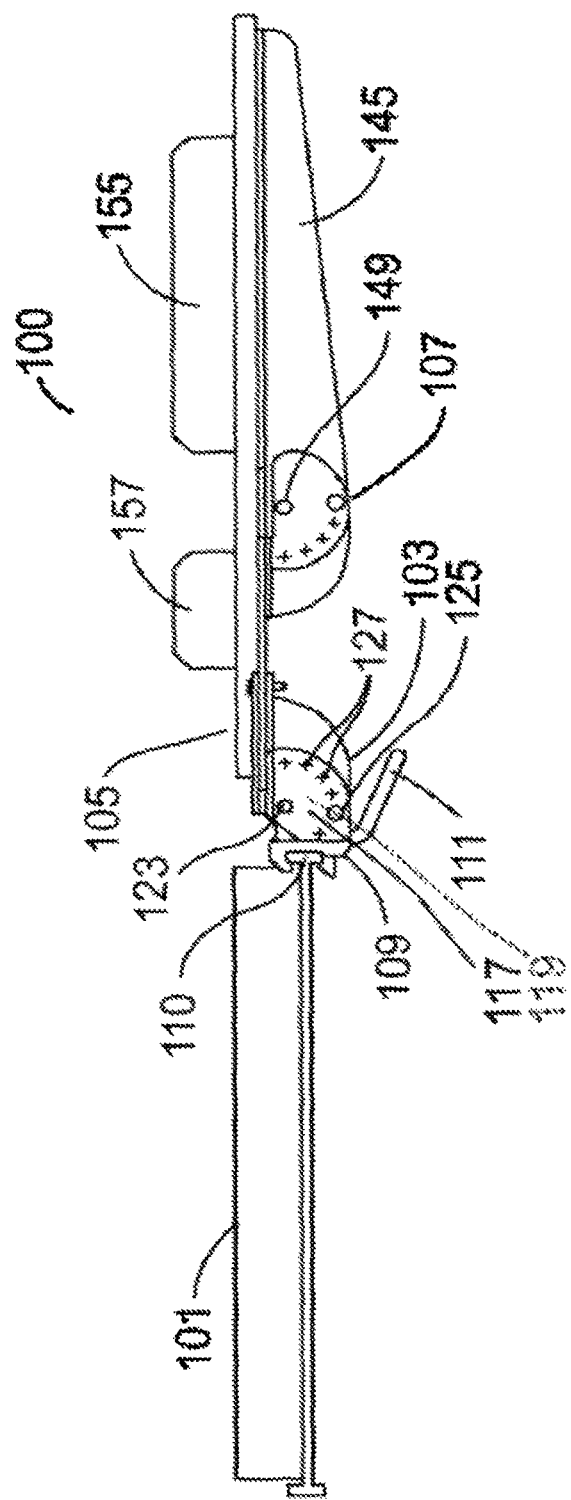

Unless otherwise indicated illustrations in the figures are not necessarily drawn to scale.

DETAILED DESCRIPTION OF THE PREFERRED EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be understood that any exact measurements/ dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

The current class of radiolucent materials is comprised of the following non-limiting examples: Carbon Fiber, Polyethylethylketones (PEEK), DELRIN acetal polymer, TORLON polyamide-imide, PES Carbon Composite, as well as a plethora of other high performance polymers such as, but not limited to, Polyphenylene Sulfides, Polyetherimides, and Polyaryletherketones, as well as an array of emerging carbon fiber reinforced thermoplastic and polymer composites. Generally, these materials are quite brittle and prone to mechanical failure under conditions of sustained load bearing. Such radiolucent materials, when constructed in sufficient thicknesses so as to provide the necessary strength for anatomic support functions, typically become sources of density artifacts themselves, or when constructed as anatomic load bearing supports in such a way as to eliminate said density artifacts, become mechanically unstable or prone to breakage due to their inherently brittle characteristics. The overwhelming preponderance of existing anatomic support structures that claim to be radiolucent utilize non-ferromagnetic metal components at the joints or as support columns in order to overcome these stated deficiencies and limitations presented by the properties of said radiolucent materials presently available. In instances where non-metallic support solutions have been offered, the structures are limited in terms of load bearing and radiolucent properties and have proven prone to breakage.

A practical embodiment of the present invention pertains to a method of fashioning mechanisms and apparatuses for variable intra-operative and diagnostic radiolucent anatomic patient positioning utilizing articulating and lockable interconnecting joints. Many practical embodiments are implemented without the use of metallic components while providing sufficient strength to support a sustained load, the implementation of which can facilitate and make possible the art of articulated anatomic positioning within current and newly emerging imaging technologies such as the O-Arm and seamless interface with the next generation of operating room based open MRI imaging surgical suites. Some practical embodiments teach the fashioning of joints which utilize a narrow, interlocking male/female channels constructed of high strength laminar sheeting to replace the need for metal in the construction of an articulated joint with means for variable articulation and locking of such joints. Furthermore, some practical embodiments enable the construction of non-metallic, radiolucent anatomic support apparatuses which exhibit the full range of variable positioning throughout the entire range of the three plane (i.e., x, y, z) axes while simultaneously supporting weight bearing loads equal to those addressed by anatomic support structures utilizing metallic components.

FIGS. 1A, 1B and 1C illustrate an exemplary radiolucent anatomical positioner 100 with articulating joints, in accordance with an embodiment of the present invention. FIG. 1A is a diagrammatic side view of positioner 100 attached to a patient platform 101. FIG. 1B is a diagrammatic front view, and FIG. 1C is an exploded view. In the present embodiment, the articulating joints comprise interconnecting channels and members fashioned from high strength, rigid laminar sheeting arranged into an interlocking male/female configuration, similar to a book (i.e., male member) sliding into a slipcase (i.e., female member) with non-metallic connectors at pivot points. Said channels are fashioned in such a way as to allow the male and female members to articulate similarly to a patient's anatomical joint and to provide variable positioning along all axes (i.e., x, y, and z) in whatever number and arrangement is most applicable to the anatomical positioning solution desired.

Referring to FIG. 1A in the present embodiment, anatomical positioner 100 comprises a series of three hinged articulation points, an articulating vertical base joint 103, a pivoting horizontal joint 105 and an articulating vertical end joint 107, with locking actuated via variable insertion of non-metallic positioning pins. It is contemplated that some alternate embodiments may be implemented with more or fewer articulating joints depending on factors such as, but not limited to, the portion of the anatomy being positioned, the type of positioning solution desired, the size of the patient, etc. In the present embodiment, anatomical positioner 100 is secured to patient platform 101 via a rail attachment 109, which is a lockable channel designed to grasp a standard sized radiolucent accessory side rail 110 typical on patient platforms within imaging environments. Rail attachment 109 may be latched and unlatched via a rail latch 111 that is held in a latched position by a radiolucent spring 113. A user may depress rail latch 111 to release rail attachment 109 from side rail 110. It is contemplated that in some alternate embodiments, positioners may be implemented with various alternative means of attachment such as, but not limited to, various clamps, slotted members, friction pads, vise-like arrangements, bolts, screws, etc.

Referring to FIG. 1C in the present embodiment, vertical base joint 103 comprises an interior load bearing vertical support member 115 and two right angled supports 117 and 119 connected by an interconnecting buttress member 121. Interconnecting buttress member 121 creates space between right angled supports 117 and 119 into which load bearing vertical support member 115 is inserted. Referring to FIG. 1A, right angled supports 117 and 119 are connected to load bearing vertical support member 115 by a fixed pivot connection point 123 and an adjustable connection point 125. Load bearing vertical support member 115 and right angled supports 117 and 119 comprise multiple holes 127 into which the connection means (e.g., pin, bolt, screw, etc.) of adjustable connection point 125 may be inserted. This enables right angled supports 117 and 119 to rotate between a horizontal position and a vertical position and to be locked in place at multiple points between these positions.

Referring to FIG. 1C, horizontal joint 105 comprises a fixed support member 129, which is attached to right angled supports 117 and 119, and a rotating support member 131, which is movably attached between fixed support member 129 and right angled supports 117 and 119 by a fixed pivot connection point 133. Rotating support member 131 rotates about pivot connection point 133 and can be locked in place by a locking member being inserted into an adjustment hole 135 on rotating support member 131 and one of a multiplicity of adjustment holes 137 on fixed support member 129. The end of rotating support member 131 opposite connection point 133 comprises a multiplicity of attachment holes 139 to which two right angled supports with interconnecting buttress members 141 and 143 may be attached. Two limb supports with interconnecting load bearing vertical support members 145 and 147 connect to right angled supports with interconnecting buttress members 141 and 143 at vertical end joint 107. Referring to FIGS. 1A and 1C, a fixed pivot connection point 149 holds these members together and enables limb supports with interconnecting load bearing buttresses 145 and 147 to rotate between a horizontal position and a vertical position. An adjustment hole 151 enables locking means to be inserted into right angled supports with interconnecting buttress members 141 and 143 and then into one of a multiplicity of adjustment holes 153 on limb supports with interconnecting load bearing buttresses 145 and 147 to hold these members at a chosen angle.

In the present embodiment, the various male and female interconnecting laminar members can be variably positioned and made to maintain said position via a means of temporary securement for purposes of variable positioning and adjustable fixation of anatomical positioner 100. To accomplish this, some of the members of positioner 100 comprise a series of small circular holes arranged within the male and female interconnecting laminar sheets with locking and unlocking effected by the insertion and removal of a non-metallic positioning pin through both the male and female members as a means to retard further motion. Those skilled in the art, in light of the teachings of the present invention, will readily recognize that a multiplicity of suitable means of locking and unlocking the joints may be used in some alternate embodiments including, but not limited to, friction, toothed gears, pneumatic means, other mechanical means, etc. In one alternative embodiment, the locking means may be effected via an internal system of pulleys constructed from radiolucent Kevlar (i.e., Mountaineering) rope and threaded both thru and around the rim of the vertical support member such that the flexor and tensor functions of the joint may be effected via the variable motion of the rope in the manner of an artificial muscle with means of securement of said lock provided by a windlass or spool in the manner of a lockable reel. In other alternative embodiments, the means of locking and securing the joint may be affected via the interposition of a PEEK spring actuator enclosed in a housing. Said housing equipped with an internal slotted mechanism interfacing with said Peek spring actuator so that the joint locks automatically when released after having been manipulated into optimum positioning.

In the present embodiment, anatomical positioner 100 is constructed of laminar sheets of radiolucent carbon fiber. In some alternate embodiments, the same method of construction may be applied to various different materials such as, but not limited to, Poly Ethyl Ethyl Ketone (PEEK), exotic materials as are presently available or as will present in future, etc. Furthermore, the present embodiment describes flat laminar sheeting connected to the articulating joints to provide support to various portions of a patient's anatomy such as, but not limited to, arms, legs and heads. It is contemplated that in some alternate embodiments, various different means of support may be provided, including, but not limited to, rods, sheets, cylinders, tubes, tube like sections, assemblies, arches, etc. In addition, in some alternate embodiments the support members may be adjustable in length and/or width Referring to FIGS. 1A and 1B, limb supports 145 and 147 comprise padding 155 and fixed support member 129 comprises padding 157. Padding 155 and 157 is made of radiolucent positioning foam shaped ergonomically to the anatomic feature to be positioned. Padding 155 and 157 is also contained within a hypo-allergenic sheeting material. Those skilled in the art, in light of the teachings of the present invention, will readily recognize that a multiplicity of suitable means of padding may be used in some alternate embodiments such as, but not limited to, memory foam, gel pads, liquid filled bladders, disposable or non-disposable fabric, non-fabric sheathing, rubber sleeves, padded sleeves which slip over the entire apparatus and are fitted with straps to retain anatomic portions, hook and loop attached radiolucent foam forms fitted with straps to retain anatomic portions, padded straps which wrap circumferentially around the apparatus, etc. Other alternate embodiments may be implemented without padding. Some embodiments of the present invention also comprise means of securing the patient's anatomy to the positioner such as, but not limited to, straps comprising hook and loop material, elastic bands, foam clamshells, various different fabric closures, catchments, etc.

In typical use of the present embodiment, a user depresses rail latch 111 and attaches rail attachment 109 to accessory side rail 110 on patient platform 100. Articulating joints 103, 105 and 107 are then adjusted so that positioner 100 can hold the patient's anatomy in the desired position for example, without limitation, holding the arm out from the body with the elbow bent at a 90-degree angle or holding the leg with the hip and knee bent so that the knee is pointing upward. Locking means secure joints 103, 105 and 107 in the desired positions. The patient is then placed on patient platform 100 with the portion of the anatomy to be supported placed on positioner 100. Padding 155 and 157 provides comfort to the patient. If desired, securing means may be utilized to hold the patient's anatomy to positioner 100. Imaging of the patient may then be performed. Positioner 100 is designed to replicate the natural movement of the patient's anatomy in such a way as to facilitate placement and intra-operative anatomic positioning within the workable bore openings of state of the art 3D fluoroscopy and imaging technologies, including, but not limited to, MRIs, C-Arms, the Medtronic O-Arm, as well as emerging portable MRI devices, open MRI suites, and other technologies as yet to be introduced, as well as implementation as a either components within a patient care platform, such as, but not limited to, an operating or imaging room bed or chair, or as the main support components of an operating room bed or chair, such that the present invention acts in the manner of a variably positionable, radiolucent articulating suit of armor beneath a patient in the imaging setting, effectively replacing the need for preexisting means of patient platforms to include beds and chairs.

Positioner 100 is generally functional within the surgical and diagnostic environments and typically meets all load-bearing criteria with respect to anatomical positioning apparatuses. The present embodiment presents a means of using the combined strength of multiple articulating layers of laminar sheets of radiolucent material as a means of providing variable positioning, lockable, load bearing support and positioning of portions of the anatomy across the entire three dimensional xyz axes, as opposed to merely along the xy axes, while functioning within the magnetic and radiographic medical imaging environment. The spreading of the load bearing stress across the entire length and continuum of the laminar sheeting of the multiple components of the articulating joints has the effect of generally avoiding the susceptibility to stress fractures and load failure which the concentration of stress through the thickening of load bearing components in currently available non-metallic radiolucent anatomic positioners often leads to. Each component of the joint acts as a load bearing support upon which rests the portion of the anatomy. As such, lateral downward pressure/load bearing stress in the anatomic support plane translates into an increased compression force which presses together the segments of the joint which form the vertical support. Meanwhile, lateral stress in the vertical support translates into a firmer bond between the segments forming the vertical support and increased load bearing potential.

FIGS. 2A and 2B illustrate an exemplary articulating vertical base joint 201 and an exemplary articulating horizontal joint 203, in accordance with an embodiment of the present invention. FIG. 2A is a diagrammatic side view, and FIG. 2B is a diagrammatic top view. In the present embodiment, vertical joint 201 is able to articulate 90 degrees from a horizontal position to a vertical position, and horizontal joint 203 is able to rotate 180 degrees from parallel to the patient platform in a proximal direction to parallel to the patient platform in a distal direction. Articulating joints 201 and 203 comprise interconnecting channels and moving members fashioned from high strength, rigid laminar sheeting arranged into a male/female configurations with non-metallic connectors at central pivot points. For example, without limitation, horizontal joint 203 comprises right angled members 205 and a fixed support member 207 that create a channel 209 into which a rotating support member 211 is inserted. These members are held together at a central pivot point by a non-metallic connector 213. Referring to FIG. 2B, locking means such as, but not limited to, a non-metallic pin, may be inserted into adjustment holes 215 on fixed support member 207 to hold rotating support member 211 at a desired position.

In the present embodiment, vertical base joint 201 is configured to bisect the length of the underside of the anatomic support structure. In some alternate embodiments, joint assemblies may be configured to be positioned laterally along the length of the side of the anatomic support structure, similar to the manner of positioning joints in a suit of armor, whereby the joint design is repositioned at the lateral aspect of the natural anatomic joint as opposed to directly beneath the natural anatomic joint. In other alternate embodiments, the joint may be placed in various different locations such as, but not limited to, offset from the center of the underside of the support structure, on top of the support structure, etc.

FIG. 3 is a diagrammatic side view of an exemplary articulating vertical joint 301, in accordance with an embodiment of the present invention. In the present embodiment, a right angled support with interconnecting buttress member 303 is attached to a limb support member 305 by a non-metallic pin inserted into a central pivot point 307. Locking means inserted into an adjustment point 309 on right angled support with interconnecting buttress member 303 corresponds to a multiplicity of adjustment holes (not shown) on limb support member 305 to lock limb support member 305 in one of a multiplicity of positions. Vertical joint 301 is able to articulate 90 degrees from a horizontal position to a vertical position and can be locked in various different positions between these positions.

Figure 4A:
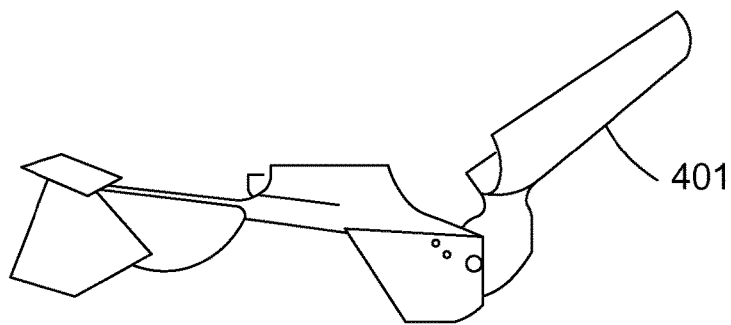
FIGS. 4A through 4G illustrate an exemplary radiolucent anatomical positioner in a variety of positions, in accordance with an embodiment of the present invention.
Figure 4B:
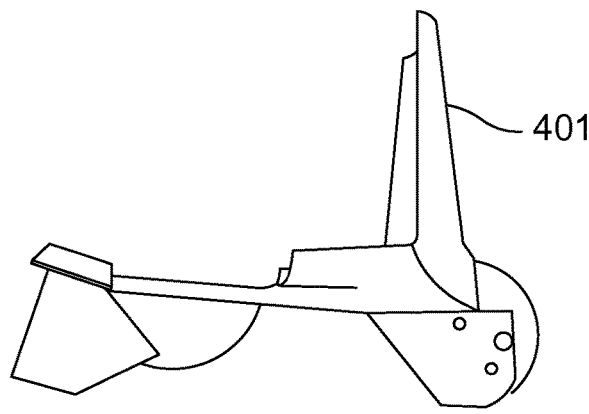
Figure 4D:
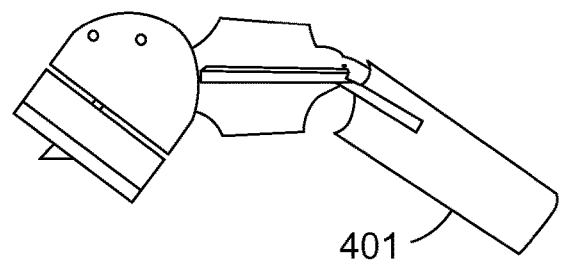
Figure 4C:
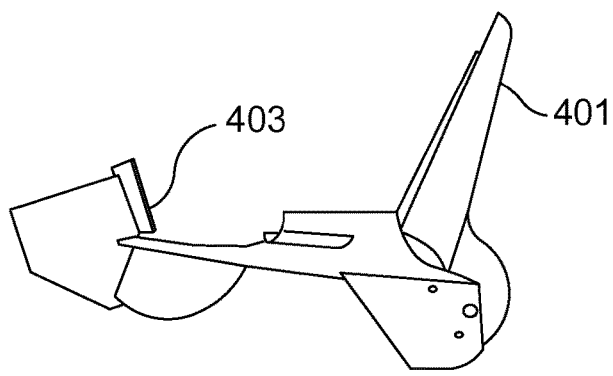
Figure 4E:
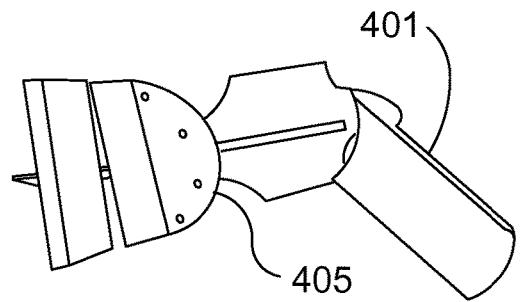
Figure 4G:
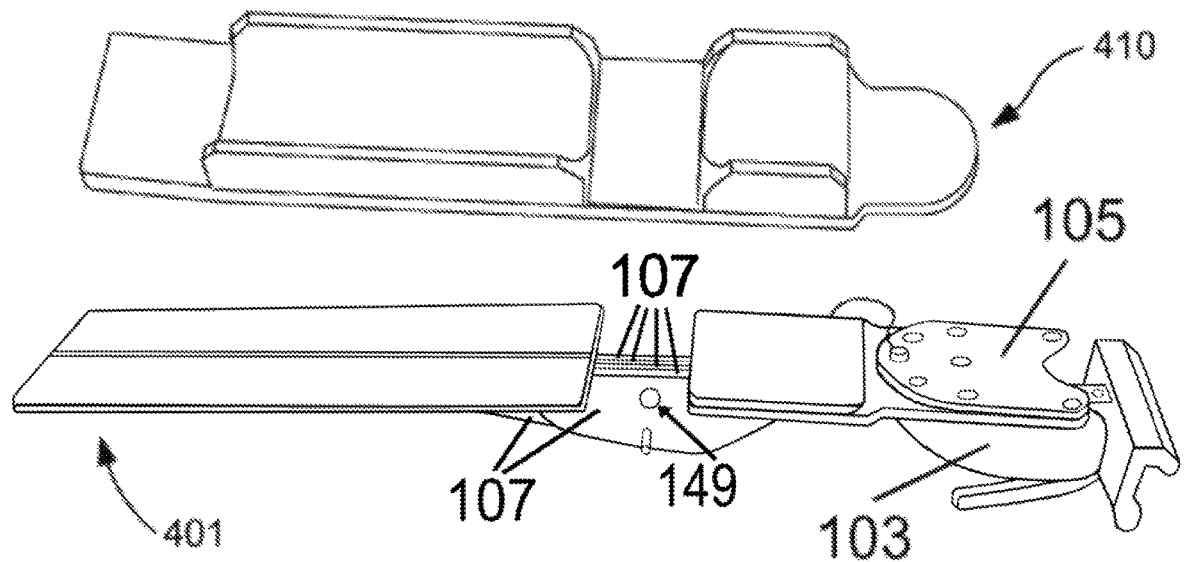
Figure 4F:
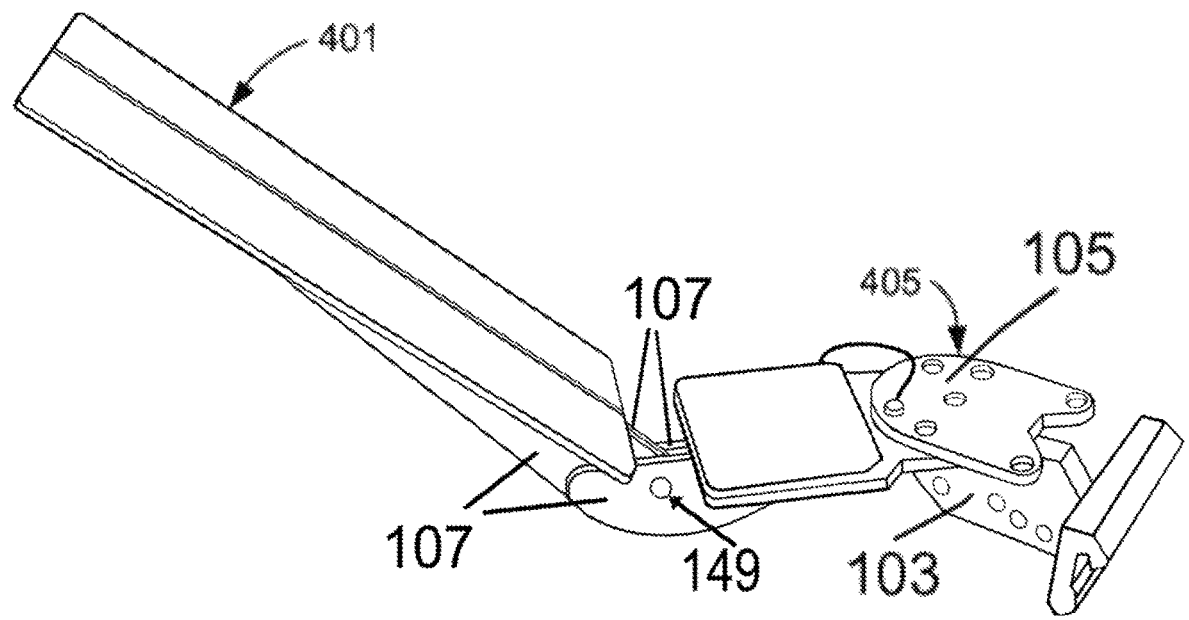

FIGS. 4A through 4G illustrate an exemplary radiolucent anatomical positioner in a variety of positions, in accordance with an embodiment of the present invention. FIG. 4A is a side view of the positioner with a limb support 401 in a partially raised position. FIG. 4B is a side view of the positioner with limb support 401 raised to a 90-degree angle. FIG. 4C is a side view of the positioner with limb support 401 in a raised position and a base joint 403 articulated to a near 90-degree angle. FIG. 4D is a top view of the positioner with limb support 401 in a raised position. FIG. 4E is a top view of the positioner with limb support 401 in a raised position and a horizontal joint 405 rotated to the right. FIG. 4F is a top view of the positioner with limb support 401 in a raised position and a horizontal joint 405 rotated to the left. FIG. 4G is a top view of the positioner with limb support 401 in a flat position and padding 410.

The exemplary anatomical positioners illustrated by way of example in the foregoing were related to upper extremity limb positioners. However, alternate embodiments of the present invention may be implemented as various different types of anatomical positioners and are not limited to the specific lengths, dimensions, number of joints, etc. illustrated by way of example in the foregoing embodiments. It is contemplated that those skilled in the art, in light of the teachings of the present invention, will readily recognize that the usage of high strength laminar sheeting in the construction of lockable radiolucent articulating joints may be implemented with regards to the construction of non-metallic, variably articulated and lockable radiolucent positioning aids in various different shapes and sizes and with various different numbers of joints for use with virtually any portion of the anatomy. For example, without limitation, some alternate embodiments may be implemented as an anatomic load bearing support for a lower extremity, as a neurosurgical head support, or as a hip positioner, all with full spectrum applicability to the entirety of magnetic and radiographic imaging environments. In some alternate embodiments, the radius of the vertical support members and buttresses can be increased to be configured for up to 360 degrees of rotation. As such, the articulating joint design can be combined into various different supports and positioners and can be placed laterally to the anatomical joint, as opposed to medially.

The embodiments described and illustrated by way of example in the forgoing comprise flat laminar sheets of radiolucent material configured as the means of anatomic support which may or may not be configured to accommodate various shaped, low-density (i.e., radiolucent) pads which have been curved or fashioned to mirror the parameters of specific anatomic shapes. In some alternate embodiments, the flat laminar sheets may be fashioned as simple planes, as truncated cylinders, as segments of parabola, or as various other more complex shapes and size as would be deemed applicable to one skilled in the art in light of the teachings of the present invention. Additionally, some alternative embodiments may include, without limitation, a series of open ended, flat concentric adjustable rings or ring segments configured to work in concert with various shaped low-density (i.e., radiolucent) pads which are curved or fashioned to mirror the parameters of specific anatomic shapes. Other alternate embodiments may comprise a multiplication of the method of interlocking male and female laminar sheets via an arrangement of any number of said articulating joints working in tandem and in varying sizes and arrangements, so that these interlocking joints might be arranged side by side in the manner of the blades of a threshing machine, or fashioned in such a manner as to scissor much like the blades of a hinged shrubbery trimmer. Other alternative embodiments may do away with the laminar sheets in favor of the usage of corrugated members as the solution to reduction of density artifact, or may alter the method of usage of flat laminar sheets via the introduction of eccentric curvature to these sheets in the manner of leafs or petals, thereby emulating nature, and yet essentially working within the method as herein introduced. In other alternative embodiments, fenestrations or openings may be introduced to either the laminar sheets utilized in the exemplary embodiment or to other members, which may replace the laminar sheets. In another embodiment of the present invention the laminar sheets are given support via movable structures placed beneath said articulating laminar sheets in the manner of shadow puppetry, wherein adjustable length tubes, rods or members provide the load bearing support, or via the usage of load bearing radiolucent cables, strings, slings or various other rigid or non-rigid assemblages suspended via an armature from above, in the manner of marionette puppetry; puppetry being an excellent description of said alternative embodiments, in that puppetry, like the present invention, deals with the support and positioning of articulated anatomic members. In other alternative embodiments of the present invention, a series of nested, overlapping cylindrical segments constructed so as to articulate in the manner of a centipede's exoskeleton utilizing the an articulating joint beneath the anatomic joint or lateral to the anatomic joint. Yet other alternate embodiments may replace the articulating joint with a lockable spool/windlass utilizing the strength and radiolucent qualities of Kevlar mountaineering rope as both flexor and tensor threaded thru semi cylindrical articulating radiolucent exoskeleton segments. Still other alternative embodiments may replace the articulating joint with a piston or interconnecting assemblage of male female components arranged along the side of the natural anatomic joint, such that the variable elongation or shortening of the total length of the piston like male and female assembly would result in a replication of the flexor tensor operation of the anatomic joint, such a piston like arrangement may be actuated via an internal radiolucent pulley, such that operation of a spool/windlass would lengthen or shorten said piston. Other alternative embodiments may include various other methods of actuating the lengthening and shortening of said male female piston like assemblies, said piston relying upon it's own internal strength for load bearing, or utilizing methods of load bearing and positioning based upon the aforementioned marionette and or shadow puppetry based solutions. Other alternative methods utilize flat and or eccentrically shaped laminar sheets as the piston like mechanism, said lockable and interconnecting laminar sheets adjustable in length in the manner of a man's belt threading thru various forms of buckle, and connected to the anatomic supports via either a slotted channel or a flat spool revolving on a center point, thereby allowing replication of the articulated hinge function while still offering no density artifact. Still other alternative embodiments of the present invention replace the articulating hinge with an overlapping series of male female members in the manner of two hands spreading their fingers and interconnecting, thereby emulating the natural hinge mechanism of an anatomical joint. Said "holding hands" method of interconnecting finger like protrusions may be variably positioned and locked via the interaction of lateral thumb-like mechanisms. Said thumb like mechanisms may communicate in the manner of a piston, a slotted belt like assembly configured from laminar sheeting, or via interaction with a rotating flat spools situated at the lateral end of the assembly. Such an alternative embodiment of an articulating hinge would mirror the action of two hands locked in the prayer position, with scissoring thumb like structures interacting as an adjustable component, and would thereby replicate the 180 degree function of a natural anatomic joint while exhibiting much improved radiolucent properties and may be constructed of laminar sheets of radiolucent material.

Those skilled in the art, in light of the teachings of the present invention, will readily recognize that non-metallic, high strength, low attenuation articulating joints in some alternate embodiments may be implemented in a multiplicity of suitable fields outside of the environments of magnetic and radiographic imaging such as, but not limited to, in the fields of military and non-military aviation as a means of actuating aerodynamic control surfaces, as well as equivalent practical application to military stealth technology, as a mechanical actuator for implementation in aircrafts, seacrafts, spacecrafts and land-crafts, etc. In aerospace, such hinges could be utilized within the designs of exploratory or surveillance platforms housing delicate sensing arrays, the operations of which would otherwise be disrupted by proximity of high attenuation metallic interference. Various other alternate embodiments may be implemented in different fields such as, but not limited to, other medical applications, electronics, computing systems, etc.

Furthermore, those skilled in the art, in light of the teachings of the present invention, will readily recognize that at least some the foregoing embodiments may be readily configured to generally support a multiplicity of body parts, including, but not limited to, a limb, a head, as a lateral support during hip revision arthroplasty, etc. Similarly, some embodiments may also be configured as a general object support, which may be useful when the object/equipment must be used with a body part being imaged during medical imaging whereby the radiolucent properties of the object/equipment support apparatus is important.

Furthermore, those skilled in the art, in light of the teachings of the present invention, will readily recognize that at least some the foregoing embodiments may be readily (re)configured and properly combined to achieve a replacement for a conventional surgical bed or chair.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Having fully described at least one embodiment of the present invention, other equivalent or alternative methods of providing articulating, radiolucent positioners according to the present invention will be apparent to those skilled in the art. The invention has been described above by way of illustration, and the specific embodiments disclosed are not intended to limit the invention to the particular forms disclosed. For example, the particular implementation of the positioner may vary depending upon the particular type of support means used. The positioners described in the foregoing were directed to implementations that are attached to platforms; however, similar techniques are to provide stand-alone articulating positioners that are supported by radiolucent stands or bases, articulating positioners that rest on top of platforms, positioners that hang from walls, ceilings or beams, etc. Implementations of the present invention that are not attached to a platform are contemplated as within the scope of the present invention. The invention is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. A rotatable joint, comprising:
   a rotatable joint portion made from radiolucent laminar sheeting, having variable angular articulation, and further including:
   a buttress member including a buttress planar portion;
   an anatomic support member including an anatomic planar portion;
   a radiolucent connection point, where the anatomic planar portion is pivotably attached to the buttress planar portion to provide rotation of the anatomic support member; and
   where the buttress member and the anatomic support member are operable to receive the load forces.

2. The rotatable joint of claim 1, where the anatomic support member and buttress member are configured for up to 360 degrees of rotation.

3. The rotatable joint of claim 1, where the radiolucent connection point further comprises a pin.

4. The rotatable joint of claim 3, where the pin is non-metallic.

5. The rotatable joint of claim 1, where the radiolucent connection point further comprises a bolt.

6. The rotatable joint of claim 5, where the bolt is non-metallic.

7. The rotatable joint of claim 3, where the radiolucent connection point is fixed.

8. The rotatable joint of claim 3, where the radiolucent connection point is adjustable.

9. The rotatable joint of claim 1, where the radiolucent connection point includes a means for connecting the anatomic planar portion with the buttress planar portion.

10. The rotatable joint of claim 1, further comprising a horizontal joint including a fixed support member and a rotating support member, where rotating support member is movably attached to fixed support member.

11. The rotatable joint of claim 10, where the horizontal joint is configured for 180 degrees of rotation.

12. The rotatable joint of claim 10 where the horizontal joint is connected to the rotatable joint portion 107 at the buttress member.

13. The rotatable joint of claim 12 where the horizontal joint is operable to rotate in a first plane, and the rotatable joint portion 107 is operable to rotate in a second plane.

14. The rotatable joint of claim 1, where the rotatable joint portion is constructed of material from the group consisting of Magnetic resonance imaging (MRI), Computer assisted Tomography (CAT/CT scan), Positron Emission Tomography, Cone beam computer assisted Tomography, Fluoroscopy, and X-ray.

15. The rotatable joint of claim 1, where the rotatable joint portion is substantially non-metallic.

16. The rotatable joint of claim 15, where the material that forms the substantially non-metallic portion of the rotatable joint portion is selected from the group consisting of Polyethylethylketones (PEEK), DELRIN acetal polymer, TORLON polyamide-imide, PES Carbon Composite, high performance polymers, Polyphenylene Sulfides, Polyetherimides, Polyaryletherketones, carbon fiber reinforced thermoplastic, and polymer composites.

17. The rotatable joint of claim 1, where the radiolucent laminar sheeting includes carbon fibers composites.

18. The rotatable joint of claim 1, where the rotatable joint portion does not cause substantial imaging artifacts.

19. The rotatable joint of claim 1, where the buttress member of the rotatable joint portion is at least medically imaging radiolucent.

20. The rotatable joint of claim 1, where the anatomic support member of the rotatable joint portion is at least substantially radiolucent.

21. The rotatable joint of claim 1, operable to provide magnetic images for intra-operative or diagnostic uses.

22. A rotatable hinge for use in an anatomic positioning system, comprising:
a male joint member and a female joint member made from radiolucent laminar sheeting where the male and female joint members configured such that the male joint member interlocks and rotates within the female joint member about a radiolucent pivot connection point;
the male joint member operable to rotate at least 90%; and
the male joint member is operable to receive load forces.

23. The rotatable hinge for use in the anatomic positioning system of claim 22, where the radiolucent pivot connection point further comprises a pin.

24. The rotatable joint of claim 23, where the pin is non-metallic.

25. The rotatable joint of claim 22, where the radiolucent pivot connection point further comprises a bolt.

26. The rotatable joint of claim 25, where the bolt is non-metallic.

27. The rotatable joint of claim 22, where the radiolucent pivot connection point is fixed.

28. The rotatable joint of claim 22, where the radiolucent pivot connection point is adjustable.

29. The rotatable hinge for use in the anatomic positioning system of claim 22, where the radiolucent pivot connection point includes a connection means.

30. The rotatable hinge for use in the anatomic positioning system of claim 23, where the female joint member is operable to receive load forces.

31. The rotatable hinge for use in the anatomic positioning system of claim 23, where the male and female joint members are made with carbon fiber composites.

32. The rotatable hinge for use in the anatomic positioning system of claim 23, further comprising a planar joint including a fixed support member and a rotating support member, where rotating support member is movably attached to fixed support member.

33. The rotatable hinge for use in the anatomic positioning system of claim 27, where the horizontal joint is configured for 180 degrees of rotation.

34. The rotatable hinge for use in the anatomic positioning system of claim 27 where the horizontal joint is connected to the female joint member.

35. The rotatable hinge for use in the anatomic positioning system of claim 28 where the horizontal joint is operable to rotate in a first plane, and the male and female joint members are operable to rotate in a second plane.

36. The rotatable hinge for use in the anatomic positioning system of claim 23, where the male joint member includes a first radiolucent laminar sheet, and the female joint member includes a second radiolucent laminar sheet, where the first radiolucent laminar sheet is configured to mate with the second radiolucent laminar sheet and the first and second radiolucent laminar sheets rotate on a common axis thereby enabling the male joint members to be load bearing.

37. The rotatable hinge for use in the anatomic positioning system of claim 23, where the male joint member includes a first radiolucent laminar sheet, and the female joint member includes a second radiolucent laminar sheet, where the first radiolucent laminar sheet is configured to mate with the second radiolucent laminar sheet and the first and second radiolucent laminar sheets rotate on a common axis thereby enabling the female joint members to be load bearing.

38. The rotatable hinge for use in the anatomic positioning system of claim 23, further including first radiolucent laminar sheeting in a first plane and second radiolucent laminar sheeting in a second plane, where the first radiolucent laminar sheeting comprises a first laminar sheet and the second radiolucent laminar sheeting comprises a second laminar sheet, and where the first and second laminar sheets are configured to be parallel.

39. The rotatable hinge for use in the anatomic positioning system of claim 23, further comprising a joint braking mechanism, where the male joint member and the female joint member are engaged together such that they rotate relative to one another, the joint braking mechanism being configured with such that the male and female joint members can be secured in a fixed position.

40. A rotatable joint for variable angular articulation made from radiolucent laminar sheeting, comprising:
- a first portion of the rotatable joint in a first plane;
- a second portion of the rotatable joint in a second plane;
- a fixed radiolucent connection point including an axis and located on the first portion and the second portion, where the first portion is operable to rotate on the axis passing through the first and second planes; and
- where the rotatable joint is further operable to directly accept load forces.

41. The rotatable joint for variable angular articulation made from radiolucent laminar sheeting of claim 40, where the fixed radiolucent connection point further comprises a non-metallic pin.

42. The rotatable joint for variable angular articulation made from radiolucent laminar sheeting of claim 40, where the first plane of the first portion of the rotatable joint and the second plane of the second portion of the rotatable joint are substantially parallel.

43. The rotatable joint for variable angular articulation made from radiolucent laminar sheeting of claim 40, where the first portion of the rotatable joint is operable to accept load forces.

44. The rotatable joint for variable angular articulation made from radiolucent laminar sheeting of claim 40, where the second portion of the rotatable joint is operable to accept load forces.

45. The rotatable joint for variable angular articulation made from radiolucent laminar sheeting of claim 40, where the first portion of the rotatable joint and the second portion of the rotatable joint receive load forces equally.

46. The rotatable joint for variable angular articulation made from radiolucent laminar sheeting of claim 40, where the first portion of the rotatable joint and the second portion of the rotatable joint are configured to rotate up to 360 degrees.

47. The rotatable joint for variable angular articulation made from radiolucent laminar sheeting of claim 40, where the first portion and the second portion of the rotatable joint lie in substantially the same plane.

48. The rotatable joint for variable angular articulation made from radiolucent laminar sheeting of claim 40, where the radiolucent laminar sheeting does not cause substantial imaging distortion or degradation.

* * * * *